United States Patent [19]

Talonn et al.

[11] 4,417,574

[45] Nov. 29, 1983

[54] LIQUID DRAIN FOR PATIENT BREATHING APPARATUS

[75] Inventors: Daniel A. Talonn, University City, Mo.; Robert E. Phillips, Studio City, Calif.; Alan B. Ranford, Des Peres, Mo.

[73] Assignee: Sherwood Medical Company, St. Louis, Mo.

[21] Appl. No.: 373,940

[22] Filed: May 3, 1982

[51] Int. Cl.³ .......................................... A61M 16/00
[52] U.S. Cl. .............................. 128/205.12; 210/490; 210/500.2
[58] Field of Search .................. 128/205.12, 725; 210/436, 500.2, 490

[56] References Cited

U.S. PATENT DOCUMENTS

| | | | |
|---|---|---|---|
| 3,556,305 | 1/1971 | Shorr | 210/490 |
| 3,603,313 | 9/1971 | Arblaster | 128/275 |
| 3,968,812 | 7/1976 | Eross | 137/188 |
| 4,221,381 | 9/1980 | Ericson | 272/99 |
| 4,249,000 | 2/1981 | Batzer et al. | 210/500.2 |
| 4,327,718 | 5/1982 | Cronenberg | 128/205.12 |

OTHER PUBLICATIONS

MEM Medical, Inc. 11/79.
Instrumentation Industries Inc., p. 12.

*Primary Examiner*—Henry J. Recla
*Attorney, Agent, or Firm*—Stanley N. Garber; Gregory E. Upchurch; William R. O'Meara

[57] ABSTRACT

A patient breathing apparatus is disclosed which includes a liquid drain connected to receive liquid condensation. The drain includes a barrier which is water permeable and gas impermeable when wet. The barrier may be provided with a water soluble layer that is gas impermeable when dry.

12 Claims, 4 Drawing Figures

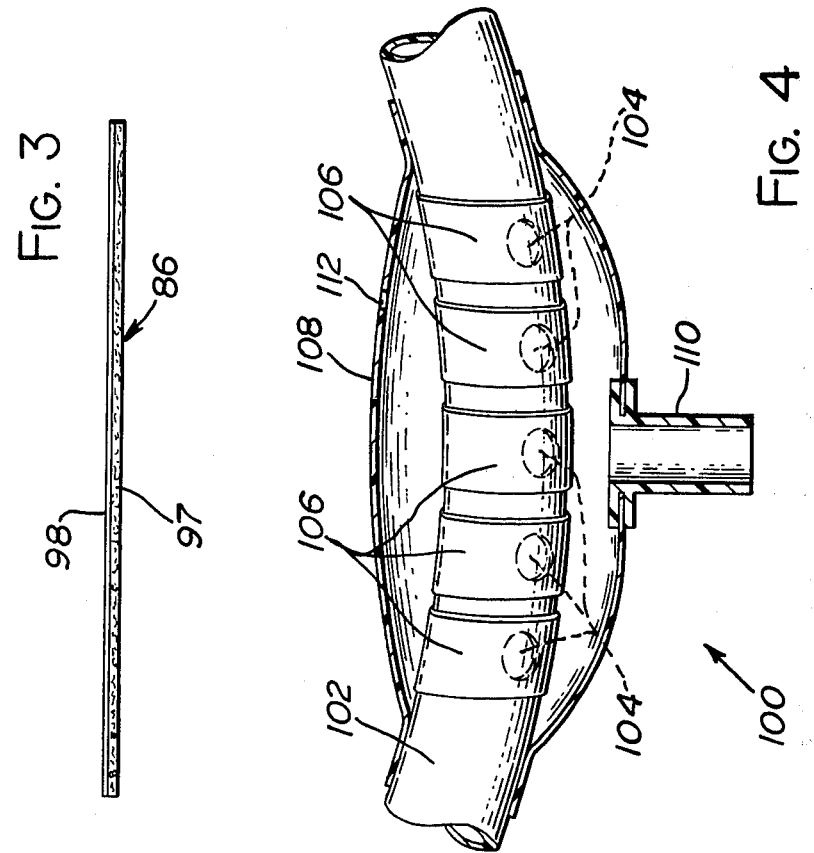
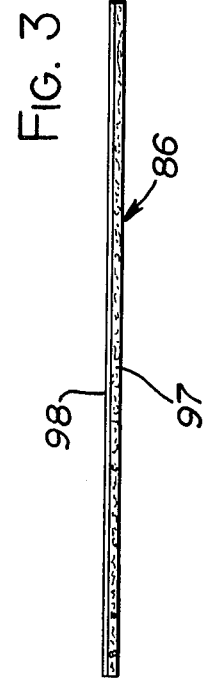
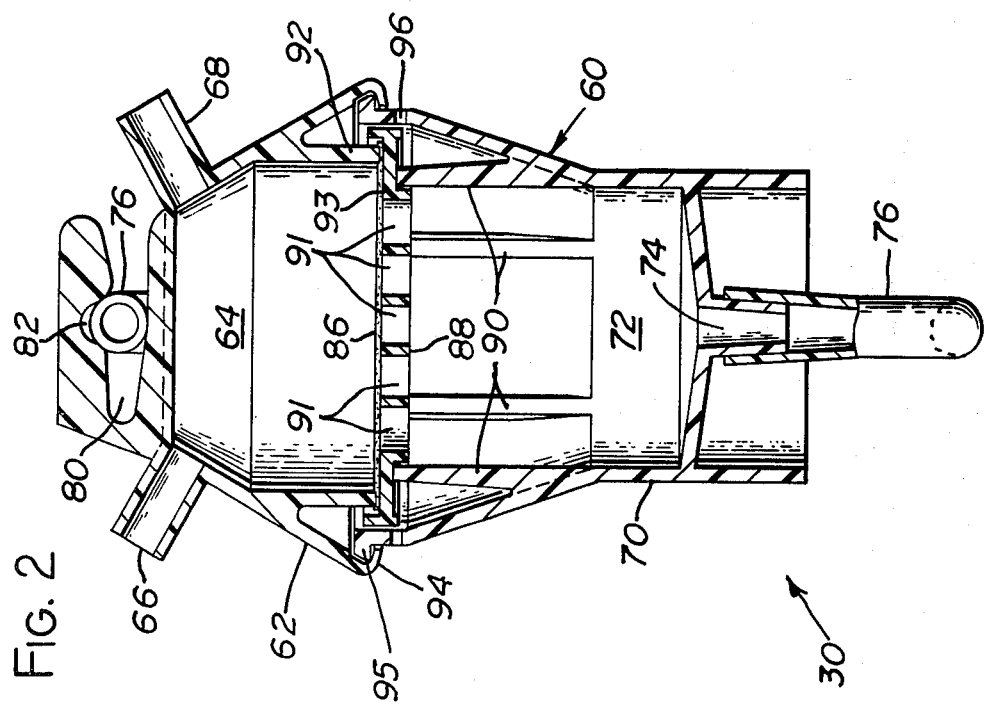

LIQUID DRAIN FOR PATIENT BREATHING APPARATUS

TECHNICAL FIELD

This invention relates to patient breathing apparatus and more particularly to a liquid drain for patient breathing apparatus.

BACKGROUND ART

As is well known, liquid or water drains or traps are employed in patient breathing systems to drain away liquid or water precipitated onto the inner sidewalls of the apparatus to prevent such liquid from pooling in low lying portions of the system and eventually entering the patient or producing an obstruction to gas flow in the system. In standard breathing systems, such as those employing a volume ventilator, for example, heated, humidified gas or air is cyclically introduced into the lungs of a patient to perform the breathing function for the patient or, in some cases, to assist the patient in breathing. In such systems, water condenses on the inner sidewalls of the breathing tubes. In some breathing systems, such as in aerosol therapy, air and a liquid such as water are used to produce a fine spray which is applied to the interior of the lungs to aid in mobilizing secretions. Medicaments such as antibiotics and bronchial medications may also be introduced by such aerosol therapy. In aerosol therapy apparatus, the liquid is precipitated in particulate form on inner sidewalls of the tubing, and a drain is used to prevent an accumulation of liquid.

Generally, in order to empty or open a water trap or drain to remove liquid or water from the breathing system without interrupting or interfering with the breathing function, various valve devices have been used. For example, a valve may be used to close a drain passage to a collection container. In such case, there is the possibility of foreign organisms entering the system because the container is removed for emptying the collected water. Also, in such cases, the container must generally be relatively small since the container normally is in fluid communication with the system gas supply and therefore adds to the system compliance or gas pressure loss of the system. The small collection container furthermore requires close attention and must be emptied often. In general, such drain valves are relatively complicated, expensive, and subject to mechanical failure.

SUMMARY OF THE INVENTION

It is an object of the present invention to provide an improved liquid drain for a system supplying gas to the lungs of a patient wherein one or more of the above-mentioned problems or disadvantages of the prior art devices are overcome.

In accordance with one aspect of the present invention, a liquid drain for a patient breathing system is provided which includes a fluid passage adapted for fluid communication with the breathing system and is subject to receive precipitated liquid of the system, and a liquid permeable, gas impermeable barrier closing the fluid passage to allow the precipitated liquid to pass through the barrier but prevent gas flow therethrough. In accordance with another aspect, a drain for a breathing system is provided with a liquid permeable barrier that is normally gas permeable when dry but which is provided with a liquid soluble, gas impermeable layer to prevent gas flow through the barrier when dry.

These, as well as other objects and advantages of the present invention, will become more apparent from the following detailed description and drawings.

BRIEF DESCRIPTION OF THE DRAWINGS

FIG. 2 is an elevational view, in cross section, on an enlarged scale, of the liquid drain of FIG. 1;

FIG. 3 is an enlarged side view of a barrier member of the liquid drain of FIG. 1; and FIG. 4 is a side view, partly in cross-section, of a liquid drain in accordance with a modified embodiment of the present invention.

BEST MODE FOR CARRYING OUT THE INVENTION

Figure 1:
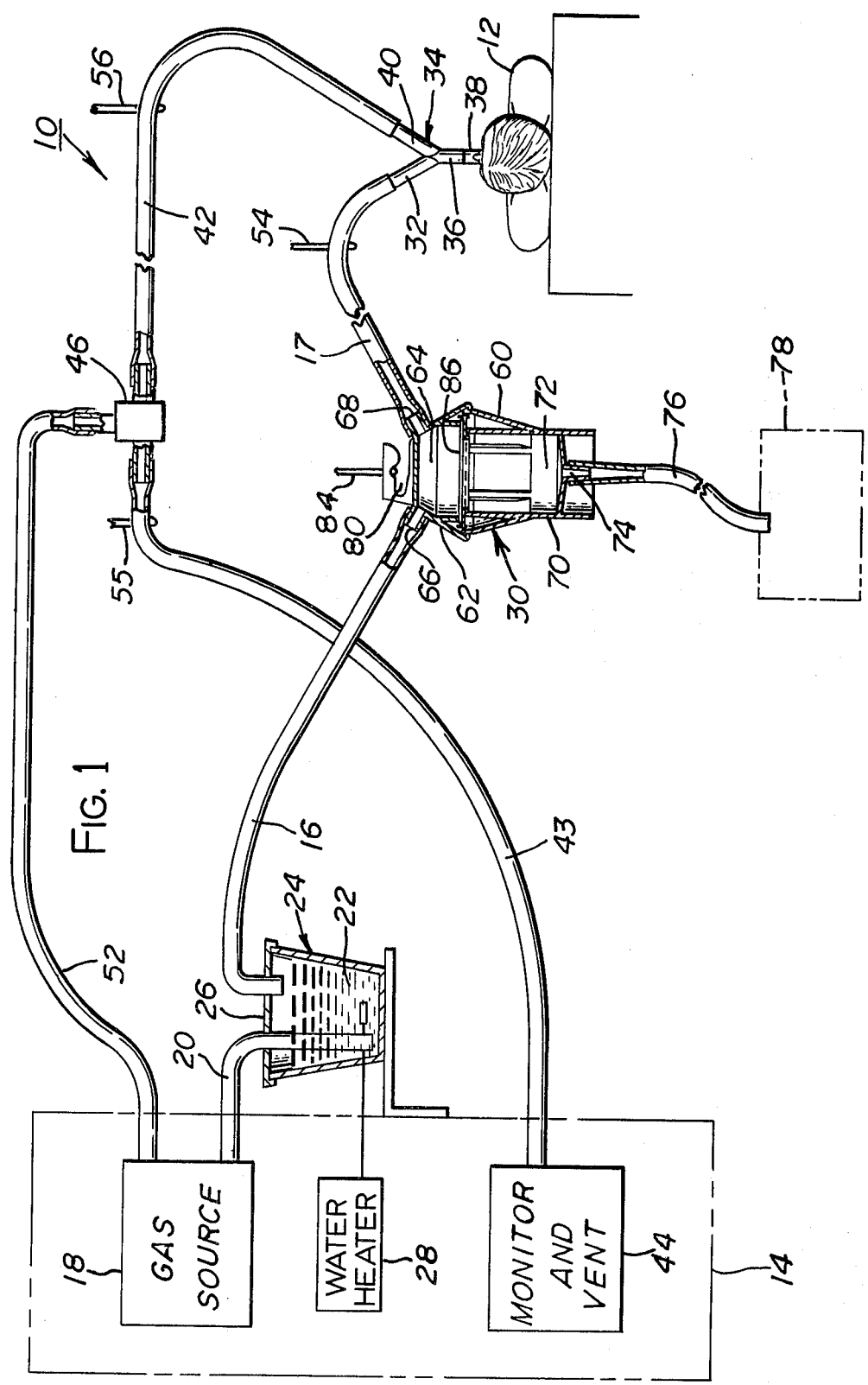
FIG. 1 is a diagramatical illustration of a patient breathing system having a liquid drain in accordance with a preferred embodiment of the present invention.

Referring now to the drawings, and particularly to FIG. 1, a breathing system 10 is shown which supplies gas or air to the lungs of a patient 12. System 10 is shown as a ventilating or patient breathing system which includes a volume ventilator 14 supplying heated, humidified gas or air to the lungs of the patient 12 through inhalation tubing including inhalation tubes 16 and 17. Ventilator 14 has a pressurized, controlled gas source indicated at 18 which may include a conventional pump and pump control circuit for supplying pressurized gas to a ventilator outlet tube 20. Tube 20 extends into a quantity of liquid such as water 22 contained in a humidifier 24. Tube 20 passes through a sealed humidifier lid 26 in air-tight relation and extends downwardly to a point near the bottom of the humidifier. Inhalation tube 16 has an inlet end extending in fluid-tight relation through the humidifier lid 26 with the open end of the tube above the level of the water 22 in the humidifier 24. A water heater 28 heats the water in the humidifier and maintains it at a relatively high temperature in order to maintain the gas reaching the patient at the temperature desired for patient breathing.

Connected in the inhalation tubing portion of the system between tubes 16 and 17 is a liquid trap or drain 30 in accordance with the present invention. Tube 17 connects with an inhalation inlet 32 of a ventilation Y-coupler 34 which has a breathing tube portion 36 connected to a conventional patient tube 38 for supplying gas from the ventilator 14 to the lungs of the patient 12. The patient tube 38 may be an endotracheal or tracheostomy tube in the system shown or it may be a mouthpiece in an aerosol therapy system.

The connector 34 also has an exhalation or outlet 40 connected to exhalation tubing including a tube 42 that connects with a tube 43 to the ventilator system, for example, through a volume monitoring and atmospheric vent circuit indicated generally at 44. A conventional exhalation valve 46 is connected in series in the exhalation tubing between tubes 42 and 43. Valve 46 is normally open to allow exhalation air or gas expelled from the lungs to flow through the valve and tubes 42 and 43 to the monitor and to the atmosphere but is automatically closed during the inhalation portion of the breathing cycle or during the pressurized or positive pressure gas application to the lungs so that the gas flows into the patient. Valve 46 may be any conventional or suitable well-known exhalation valve and is diagramatically shown simply as a pneumatically controlled valve. The valve 46 is shown for illustration as being controlled by connecting a control tube 52 to the pressurized gas source 18 so that whenever the source 18 applies a pressurized pulse of air for ventilating the patient, it simultaneously supplies a pressurized pulse of air through control tube 52 to close the valve 46 and therefore the exhalation tube 42. The source 18 allows the valve to open during the exhalation portion of the breathing cycle.

A plurality of tube-supporting hangers are indicated at 54, 55 and 56 for supporting the inhalation and exhalation tubes as they extend from the ventilator 14 to the patient 12. The inhalation and exhalation tubes generally vary in elevation between the ventilator and the patient so that there are locations along these tubes of relatively high and low elevation. Trap 30 is preferably located at a location in series with tubes 16 and 17 and at a point of relatively low elevation so that liquid, and in this case, water condensation or precipitation formed on the inner walls of the tubes 16 and 17 will tend to flow toward water drain 30. The greatest amount of condensation will generally form in tubes 16 and 17 and especially in tube 16 where the gas is at its highest temperature.

As also seen in FIG. 2, the water trap or drain 30 is shown including a hollow housing member 60 having an upper Y-shaped tube connector portion 62 providing a drain inlet passage or chamber 64. The Y-connector 62 has a pair of tube connectors 66 and 68 connected respectively to the inhalation tubes 16 and 17 (FIG. 1). Gas can freely flow through the connectors 66 and 68, and chamber 64 during the inhalation portion of the breathing cycle.

Housing 60 includes a lower, generally cup-shaped portion 70 providing a collection or liquid trap chamber 72 having a drain outlet 74 at the bottom of the chamber. A drain tube 76 is shown connected to outlet 74 and can be used to continuously drain precipitated water from collection chamber 72 into a building drain system or, as in FIG. 1, an auxillary container such as shown in phantom at 78. In FIG. 2, drain tube 76 is shown with one end connected to outlet 74 and with the other end frictionally engaged by the walls of a slot 80 formed in the top wall of Y-connector 62. An opening to the slot indicated at 82 may be used to hang the drain 30 from a support member. For example, a partially shown hook or wire 84 is shown in FIG. 1 extending from the slot 82 to support the drain 30.

A liquid permeable, gas impermeable barrier member 86 is disposed between the inlet and outlet chambers 64 and 72 of drain 30. A relatively rigid barrier support member 88 is disposed between the chambers 64 and 72 and is supported adjacent its periphery by a ribbed wall having a plurality of circumferentially spaced, generally vertically extending ribs 90 on the interior wall of lower housing portion 70. The support 88 is provided with at least one opening or passage and is shown with a plurality of drain openings or passages 91 to allow liquid to flow from the breathing system and inlet chamber 64 through barrier 86 to the outlet chamber 72. The barrier member 86 continuously covers or closes each of the passages or openings 91 against the flow of gas but not liquid, as will be discussed hereafter.

The upper housing member 62 is provided with a generally annular wall 92 which engages and bears on the upper surface of barrier 86 adjacent its periphery and which urges the bottom side of barrier 86 against a flat annular upper wall surface 93 of the support 88 to thereby seal the upper chamber 64 during operation, preventing the leakage of gas from the drain 30.

The upper housing member 62 is shown with its bottom periphery 94 formed around an outwardly extending peripheral flange 95 at the upper edge of the lower housing member 70 to fix the upper and lower housing members together. These housing members are preferably formed of a suitable, substantially rigid plastic material, such as polypropylene, polyethylene or the like. Preferably, the housing 60 is made sufficiently rigid to substantially maintain its shape under all fluid pressure conditions of the system. These members may be molded and then, when assembled, the lower periphery 94 of the upper member 62 may be thermally formed about the radial flange 95 of the bottom member 70 to connect the members together.

A vent opening 96 near the top of the collection chamber 72 allows air to escape from chamber 72 as it fills with drainage liquid during operation where water is to be collected in chamber 72. Vent 96 also allows collected liquid or water in chamber 72 to be drained such as through tube 76 when the tube is removed from its position in FIG. 2, that is, vent 96 allows air from the atmosphere to enter the chamber as the collected water is emptied from chamber 72 through the drain 74.

The barrier 86 is of a material which allows liquid to pass through it but does not allow gas to pass through it during operation of the system. For example, the barrier 86 may be made of a suitable fibrous, cellulosic, hydrophilic material such as conventional laboratory filter paper. Such filter paper is gas permeable when dry, but when wetted with a liquid or water becomes impermeable to gas at pressures below the bubble point of the paper. Thus, when a cellulosic filter paper is employed, the barrier 86 is preferably wetted before the system is completely placed into operation so that the barrier will be gas impermeable at the start. However, where desired, the system may be operated so that the system precipitation wets the barrier to thereafter prevent gas flow through it.

A preferred barrier 86 is shown in FIG. 3 and includes a layer of filter material such as a cellulosic, fibrous, hydrophilic laboratory paper 97 which is provided with a liquid or water soluble, gas impermeable dry coating or film 98, such as a dry polyvinyl alcohol (PVA) layer or film. Where the gas impermeable layer 98 is used, the barrier is gas impermeable before the barrier is wetted by precipitated water. When such a filter material is used, the precipitated water will disolve the layer or coating 98 during operation of the system and flow through the filter material 97 causing it to become wetted and therefore gas impermeable. By employing this material with the layer thereon, it is not necessary to pre-wet the barrier in order to prevent ventilation gas from flowing through the barrier and out of the device at the start of operation of the system. A dry film or sheet 98 of PVA may be heat sealed to one side of the paper 97. Also, a polyvinyl pyrrolidone (PVP) film or coating of a liquid soluble, gelatinous material may be used to coat member 97. Preferably, the upper side of the barrier 86 and radially inner side of barrier 106 are provided with the dry gas barrier layer. This tends to provide a slightly better gas barrier when dry. The barrier material should, of course, be chosen such that it will pass water at a desired flow rate and be able to withstand the gas pressures encountered in the system.

In operation, with the patient tube 38 disposed in the mouth of the patient 12, and the system connected to the volume ventilator 14, pulses of a gas, such as air or a desired mixture of oxygen and air, are supplied to the ventilator outlet tube 20 on the inhalation portion of the breathing cycle of the system. This gas is heated and humidified as it passes through the heated water 22 in humidifier 24 and into inhalation tube 16. The humidified gas passes through Y-connector 62 of drain 30, through inhalation tube 17, connector 34, and then into the tube 38 and the lungs of the patient 12. During inhalation, the ventilator source 18 supplies a pulse of gas to the exhalation valve 46 through control tube 52 to close the valve to thereby close off or prevent gas flow into the exhalation tube 42.

At the end of the inhalation pulse of air, the valve 46 is opened such as by reducing the air pressure in control tube 52 as controlled by circuit 18. Gas from the lungs is then exhaled through connector portion 40, exhalation tubes 42 and 43, valve 46, and the volume monitor and vent device 44 within the ventilator. Since the exhalation tubing will be substantially open to atmosphere through circuit 44 of the ventilator 14, there is little resistance to gas flow in the exhalation tubing so there is negligible backflow of exhalation gas into the inhalation tubing where the resistance to backflow is relatively high.

During continued operation of the ventilation system 10, water condenses especially on the inner walls of tubes 16 and 17 because of the humid, warm air flowing in the tubes. This precipitated water flows to a point of relatively low elevation such as at the location of the water drain or trap 30 in FIG. 1. Water flows into inlet chamber 64 through the barrier 86, and into the outlet or collection chamber 72. When the drain tube 76 is positioned to continuously drain condensed liquid, such as shown in FIG. 1, liquid will flow through tube 76 and into auxillary container 78 or other receiver. Where the tube 76 is connected as shown in FIG. 2, the collection chamber 72 fills and collects the liquid because the tube outlet end is above the upper level of chamber 72. As the chamber 72 fills, it displaces air from the chamber through the vent opening 96. Where desired, the drain tube 76 can be pushed further into the slit 80 to close it off or a tube clamp may be used to close the drain tube.

It is apparent that the water condensing on the inner walls of tubes 16 and 17 can continuously flow through the drain device 30 and into container 78 or other device without interrupting the breathing cycle. The collection chamber 72 can be allowed to fill and then be emptied or drained through tube 76 without interrupting the flow of gas to the patient and without disconnecting any parts of drain housing 60. Since the barrier 86 continuously maintains the passages 91 closed to the flow of gas during operation including during the draining or emptying of the drain 30, the use of a drain valve and the problems and disadvantages associated with such valves are obviated. Also, the collection chamber 72 of the lower housing portion 70 may be made as large as desired since it does not add to the system compliance or pressure loss of the system since the barrier 86 is gas impermeable.

In FIG. 4, a water drain or trap of modified construction is indicated generally at 100. Drain 100 includes a section of inhalation tubing 102 having at least one drain opening, and it is shown having a plurality of openings or holes 104 at the bottom of the tube. Barrier material 106 is shown in the form of tape strips wrapped about the holes 104 to cover all of the holes provided in the tube section 102. Portions of the tape 106 may be adhesively or otherwise secured to the surface of the tube section 102 to maintain the barrier material in sealing covered relation with the holes 104. A container 108 which may be a rigid member or a pliable plastic bag or sheath, is shown on the tube section 102 and at least covers the holes 104. The bag 108 may be sealed at each end by any suitable means, such as an adhesive or by a heat seal. The bag 108 may be provided with an outlet or drain tube, such as indicated at 110, for draining liquid from the bag 108. The tube 102 may be connected at its opposite ends to inhalation tubes 16 and 17 in place of device 30 of FIG. 1 so that inhalation gas will flow through the tubes 16, 17 and 102 from the source of gas 18 to the patient 12. These tubes may be integrally formed as a single tube.

The barrier 106 functions similarly to the barrier 86 of the water trap 30 of FIG. 1. Barrier 106 may be made of the same barrier material as barrier 86 and may be either a filter paper provided with a water soluble, gas impermeable layer, such as a polyvinyl alcohol layer, or it can be uncoated filter material. As gas flows through the tube section 102 during operation of the inhalation system, precipitated liquid or water flows through openings 104 and the barrier 106 and into the container bag 108 where such bag is used. The liquid may be allowed to flow out of outlet drain 110 and into another container or drain system if desired. One or more small vent openings indicated at 112 may be provided in the container 108 where it is made of a rigid material and if it is to be filled with liquid so that air may be displaced into the atmosphere by water condensation flowing into the container 108 and air can enter the container when being emptied. Vent 112 may not be necessary where the container 108 is made of an elastic material.

Such a system as shown in FIG. 1 may employ one or more water drains or traps, such as trap 30 or trap 100, at various low elevational locations. For example, a trap may be employed at the lowest point of exhalation tube 43 adjacent the ventilator. In both liquid drains or traps 30 and 100, the barrier closes the fluid passages (91 or 104) in the hollow conduit members 60 and 102 through which drainage liquid passes, and the barrier remains in place during operation of the system and during the draining of the system.

As various changes could be made in the above-described constructions without departing from the scope of the invention, it is intended that all matter contained in the above description and shown in the accompanying drawings be interpreted as illustrative and not in a limiting sense.

We claim:

1. A liquid drain for a patient breathing system in which gas is supplied to a patient comprising housing means including an upper hollow portion adapted for connection in fluid communication with said breathing systems and for receiving liquid precipitation from the system, a lower hollow portion adapted to receive liquid precipitation from said upper portion, and liquid permeable, gas impermeable barrier means including a first layer of hydrophilic material which is gas permeable when dry and liquid permeable and gas impermeable when wetted by a liquid, and a water soluble second layer on a side of said first layer which is substantially gas impermeable to prevent gas to flow through said barrier when said second layer is dry but is dissolvable when precipitated liquid contacts it, said barrier means being disposed between said upper and lower portions so that liquid precipitation is flowable through said barrier means to said lower portion from said upper portion but said barrier means prevents gas flow to said lower portion.

2. The drain of claim 1 wherein said first layer comprises sheet material which includes cellulosic fibers.

3. The drain of claim 1 or 2 wherein said second layer includes polyvinylalcohol.

4. The drain of claim 1 wherein said upper portion includes a pair of tube connectors for connecting said housing in series relation in the system and wherein said upper and lower portions are of relatively rigid material which substantially maintain their shape under variable gas pressure conditions of operation.

5. The drain of claim 1 further including liquid outlet means in said lower portion for draining liquid precipitation from said lower portion.

6. The drain of claim 1 or 3 wherein said second layer comprises a water soluble gelatinous film of polyvinyl pyrrolidone.

7. The drain of claim 1 further including a barrier support member having at least one opening therein supporting said barrier means in said housing means between said upper and lower portions.

8. The drain of claim 1 including conduit means for connection in fluid communication with the breathing system and adapted to have breathing gas flow therethrough, said fluid passage means extending through the sidewall of said conduit means, and said barrier being connected to said conduit means.

9. The drain of claim 8 further including container means connected to said conduit means for receiving liquid passing through said barrier.

10. A liquid drain for a patient breathing system in which gas is supplied to a patient comprising a housing having an upper hollow portion adapted for connection in fluid communication with said breathing system for receiving liquid precipitation, a lower hollow portion adapted to receive liquid precipitation from said upper portion, fluid passage means disposed between and in fluid communication with said upper and lower portions, a liquid permeable, gas impermeable barrier closing said fluid passage means so that liquid precipitation flows through said barrier to said lower portion from said upper portion but said barrier prevents gas flow to said lower portion, and liquid outlet means in said lower portion for draining liquid precipitation from said lower portion, said upper portion having an upper wall with a slot, and tube means having one end portion connectable to said liquid outlet means and the other end portion frictionally engageable in said slot to allow liquid precipitation to accumulate in said lower portion.

11. The drain of claim 10 wherein said tube means is slidable into said slot sufficiently to close said tube means.

12. The drain of claim 11 wherein said slot is angular in shape.

* * * * *